United States Patent
Zhai

(10) Patent No.: US 10,561,402 B2
(45) Date of Patent: Feb. 18, 2020

(54) MOTION IMAGING WITH MULTIPLE PARALLEL RECEIVE BEAMS

(71) Applicant: Siemens Medical Solutions USA, Inc., Malvern, PA (US)

(72) Inventor: Liang Zhai, Castro Valley, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 631 days.

(21) Appl. No.: 15/224,451

(22) Filed: Jul. 29, 2016

(65) Prior Publication Data

US 2018/0028154 A1 Feb. 1, 2018

(51) Int. Cl.
- *A61B 8/08* (2006.01)
- *A61B 8/14* (2006.01)
- *A61B 8/00* (2006.01)
- *A61B 8/06* (2006.01)
- *G01S 15/89* (2006.01)

(52) U.S. Cl.
CPC ............ *A61B 8/5207* (2013.01); *A61B 8/145* (2013.01); *A61B 8/461* (2013.01); *A61B 8/488* (2013.01); *A61B 8/06* (2013.01); *A61B 8/463* (2013.01); *A61B 8/5269* (2013.01); *G01S 15/8979* (2013.01)

(58) Field of Classification Search
CPC ....... A61B 8/5207; A61B 8/488; A61B 8/461; A61B 8/145; A61B 8/5269; A61B 8/06; A61B 8/463; A61B 8/52; G01S 15/8979
See application file for complete search history.

(56) References Cited

U.S. PATENT DOCUMENTS

| | | | |
|---|---|---|---|
| 2007/0049824 A1* | 3/2007 | Konofagou | A61B 8/08 600/437 |
| 2010/0036249 A1 | 2/2010 | Clark | |
| 2011/0054316 A1* | 3/2011 | Kristoffersen | G01S 7/52077 600/443 |
| 2015/0080730 A1* | 3/2015 | Kanayama | A61B 8/5207 600/447 |
| 2015/0245818 A1* | 9/2015 | Zhai | A61B 8/488 600/453 |

* cited by examiner

*Primary Examiner* — Sanjay Cattungal

(57) ABSTRACT

Line artifact reduction is provided in multi-beam scanning for Doppler imaging. An analytic solution uses estimated velocities for collocated receive scan lines from different transmit beams to reduce or remove the biases caused by multi-beam receive. For each location, a line or curve is fit to the estimated velocities as a function of distance of the transmit scan lines to the location. The velocity at an intercept of this line with the distance of zero (intercept with the origin) indicates the unbiased velocity. This approach allows a solution even where all of the velocity estimates have a bias with the same sign, such as due to the location being on a same side of the different transmit scan lines.

8 Claims, 5 Drawing Sheets

MOTION IMAGING WITH MULTIPLE PARALLEL RECEIVE BEAMS

BACKGROUND

The present embodiments relate to color Doppler, color flow, or other motion imaging using ultrasound. In particular, higher frame rate motion imaging is provided with reduced line artifacts.

Parallel receive beamformation may incease ultrasound imaging frame rate. However, parallel receive beamformation may introduce line artifacts in color Doppler images due to the misalignment between the transmit (tx) and receive (rx) beams. In color Doppler imaging, velocity is often calculated based on the assumption that the normal direction of the echo wavefront is aligned with the receive beam. This assumption is not always met when there is a misalignment between transmit and receive beams. The angular deviation of the normal direction of the echo wavefront from the receive beam produces biases in the velocity estimates. The receive beams on opposite sides of a transmit beam cause biases with different signs, which reveals as beam group artifacts in the image.

Spatial filtering is typically used to overcome the line artifact, but spatial filtering may degrade the resolution. When the number of parallel receive beams per transmit beam increases for more rapid scanning, the line artifact becomes more severe, and eventually may not be managed with spatial filters. Though advanced modern ultrasound systems are capable of processing a large number of parallel receive beams, line artifact limits the number of parallel receive beams in color Doppler imaging (e.g., limited to four parallel receive beams). To increase the frame rate, color images either lack details due to spatial smoothing or show too much line artifact.

In one approach to address this dilemma, estimates from overlapping beams acquired from two adjacent transmit groups are linearly interpolated. The linear interpolation of the velocity estimates may be effective when all the receive beams are well covered by the transmit beams. Complete overlap in the receive beams between adjacent transmit beam groups is used, but complete overlaps may limit the frame rate. The linear interpolation is limited to pairs of collinear receive beams. Other approaches may compound for more than two collocated receive beams and loosen the need for complete overlap of the receive beams from adjacent beam groups, but rely on combining velocity estimates with opposite signs of the bias, creating a spatial distribution requirement for the scanning.

BRIEF SUMMARY

By way of introduction, the preferred embodiments described below include methods, instructions, computer readable storage media, and systems for Doppler or flow imaging with line artifact reduction in multi-beam scanning. An analytic solution uses estimated velocities for collocated receive scan lines from different transmit beams to reduce or remove the biases caused by multi-beam receive. For each location, a line or curve is fit to the estimated velocities as a function of distance of the transmit scan lines to the location. The velocity at an intercept of this line or curve with the distance of zero indicates the unbiased velocity. This approach allows a linear regression solution even where all of the velocity estimates have a bias with the same sign, such as due to the location being on a same side of the different transmit scan lines.

In first aspect, a method is provided for color imaging with a medical diagnostic ultrasound scanner. A first sequence of transmit beams is transmitted along a first scan line in a planar region of a patient. In response to the first sequence of the transmit beams along the first scan line, a sequence of first receive beams is received along a third scan line. The third scan line is spaced away in the plane by a first distance from the first scan line and is on a first side of the first scan line. A second sequence of transmit beams is transmitted along a second scan line in the planar region of the patient. The second scan line is spaced away in the plane from the third scan line by a second distance, and the third scan line is on the first side of the second scan line. In response to the second sequence of the transmit beams along the second scan line, a sequence of second receive beams is received along the third scan line. A first velocity is estimated for a location on the third scan from the first receive beams, and a second velocity is estimated for the location on the third scan line from the second receive beams. A line or curve is fit to the first and second velocities as a function of the first and second distances. A combined velocity for the location is solved from the line or curve. An image of the patient is generated as a function of the combined velocity.

In a second aspect, a method is provided for Doppler imaging. Velocity estimates are acquired from different sequences of multiple simultaneous receive beam scanning for different ensembles of receive scan lines where the receive scan lines of the different sequences are in an overlapping region of a patient. For each location for which velocities estimates are acquired from more than one of the multiple sequences, the biases in the velocity estimates are corrected with a linear regression model. A Doppler image is generated from the bias corrected velocity estimates.

In a third aspect, a system is provided for Doppler imaging. A transmit beamformer is configured to transmit ensembles of transmit beams along each of a plurality of transmit scan lines. A receive beamformer is configured to receive multiple receive beams along receive scan lines in response to each of the transmit beams. At least one of the multiple receive scan lines responsive to one of the transmit ensembles is collocated with another of the multiple receive scan lines responsive to another of the transmit ensembles. A Doppler estimator is configured to estimate Doppler values for a collocated location from receive beams from the one transmit ensemble and from the other transmit ensemble. The Doppler values have biases, respectively, with a same sign. A processor is configured to determine a combined value from the estimated Doppler values for the collocated location. A display is configured to display a Doppler image of the combined value for the collocated location.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The line artifact when using parallel receive beams in color Doppler imaging may be dealt with, allowing improvement of frame rate while maintaining detail. The velocity estimate bias that introduces line artifact may be corrected using multiple estimates, including estimates from two or more overlapped transmit beam groups with any polarity or sign of the bias. Massive parallel receive beam-forming, such as for volume imaging, may be used in color Doppler imaging to achieve high frame rate and fine details without line artifact.

Figure 1:
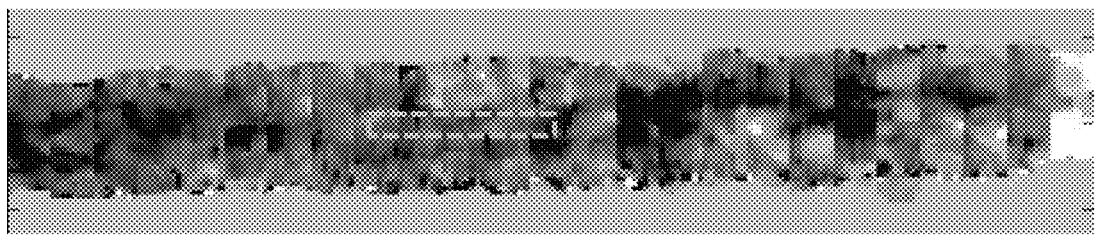
FIG. 1 is an example flow region or region of interest of a Doppler velocity image with line artifact due to multi-beam receive operation.

FIG. 1 demonstrates line artifacts in a color Doppler velocity image, presented as gray scale in the drawings. The image is a magnified extract of a tubular flow region in a color Doppler velocity image. The image is acquired on a flow phantom with a Siemens SC2000 ultrasound system and 9L4 transducer using eight parallel receive beams per transmit. No interpolation is provided. The brightness of pixels in FIG. 1 represents the estimated velocities. Line artifacts appear as the regularly spaced vertical bands. The color line artifacts are created due to misalignment between transmit and receive beams.

Figure 2:
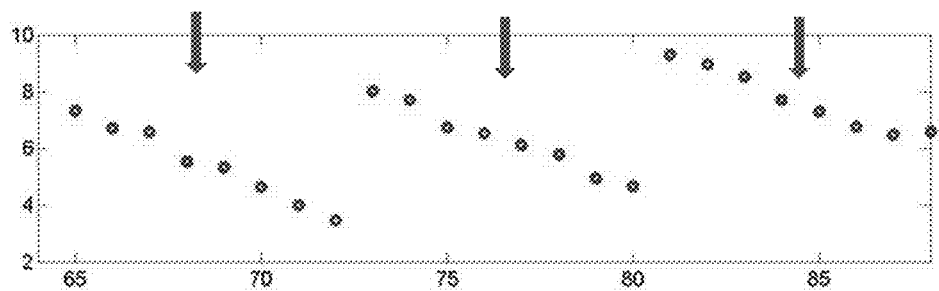
FIG. 2 shows an example of velocity bias by location for multi-beam groups.

FIG. 2 plots samples of the velocity data along the horizontal line in FIG. 1. The arrows indicate the transmit beam locations. A beam group pattern is shown in the normalized velocities. The further the receive beam is away from the corresponding transmit beam, which is indicated by the arrows, the more deviation (i.e., bias) occurs in the velocity estimate from that of the velocities for the center beams. The bias is signed, resulting in velocities for receive beams on one side of the transmit scan line being greater and velocities for receive beams on the other side of the transmit scan line being smaller. The azimuth spacing of the receive scan line locations from the corresponding transmit scan line alters the amount of bias introduced into the estimate of velocity, causing the line artifact where the bias switches sign between groups of receive scan lines.

To demonstrate the velocity bias having different signs, a receive beam located on the left side (e.g., in azimuth) of its transmit beam is labeled as a "+" beam and that on the right side is labeled as a "−" beam. Prior interpolation or averaging approaches to dealing with the line artifact rely on combining velocities from at least one "+" beam and one "−" beam at a given output location to cancel the biases. In contrast, an analytic solution may be used to combine velocities from an arbitrary number of collocated receive beams without requiring mixed "+" and "−" receive beams. A linear regression based on the estimated velocities with bias and the angle of the transmit wavefront normal to the receive scan line determines the unbiased velocity.

Bias correction may use just receive beams with the same sign (all "+" or all "−" receive beams). Velocities biased with mixed signs are not needed, so velocity estimate biases are corrected without needing collocated receive beams from opposite sides of transmit beams. When creating color Doppler imaging using multiple transmit beam groups to improve aesthetics and/or speed of scan, the beam locations that are not covered by both "+" and "−" receive beams may still be corrected. For ramp-up beams on the side of a region of Doppler imaging, this may keep frame rate high, reducing the need to transmit outside of the Doppler imaging scan region or region of interest. For scan lines near the edge, transmission and/or reception along scan lines outside of the region of interest may be avoided.

By using an analytical solution, velocities from an arbitrary number of collocated receive beams may be combined. The explicit solution may combine velocities from two or more collocated receive beams.

Figure 3:
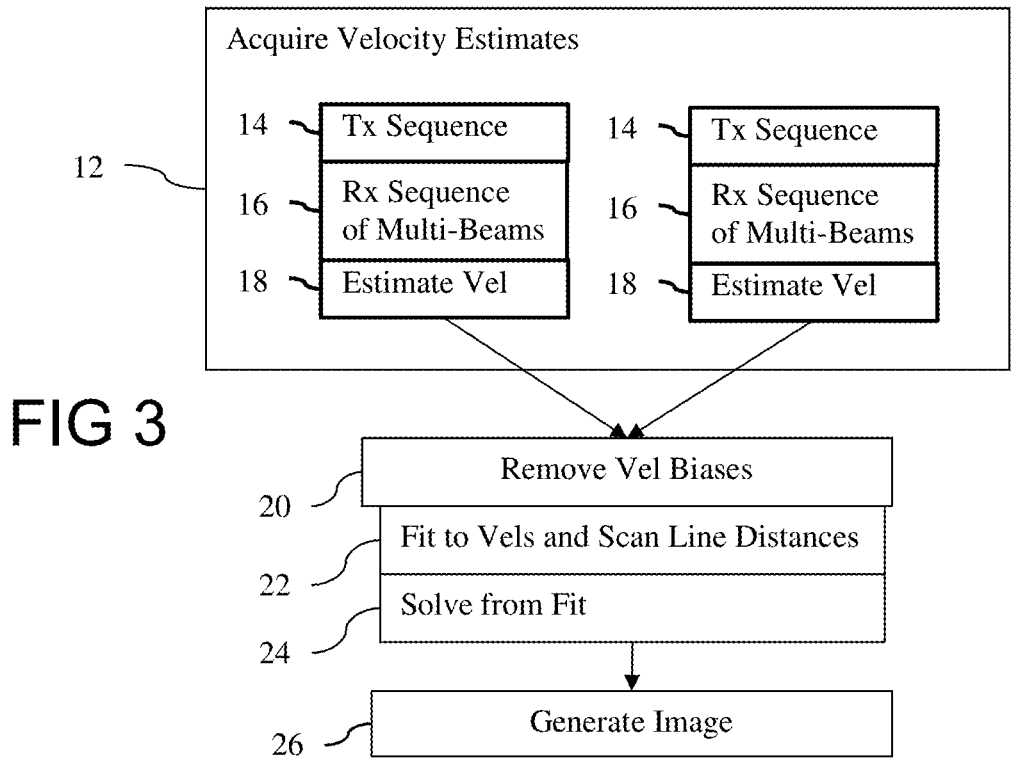
FIG. 3 is a flow chart diagram of one embodiment of a method for color imaging with line artifact reduction.

FIG. 3 shows one embodiment of a method for color imaging by a medical diagnostic ultrasound scanner. The color imaging includes multi-beam scanning with line artifact reduction. Any Doppler, flow, or color imaging may be used. By using a linear model or regression, an analytic solution removes or reduces the biases. As a result of using the analytic solution (e.g., linear regression), the corrected velocity may be determined without relying on cancellation due to biases with opposite signs.

Figure 9:
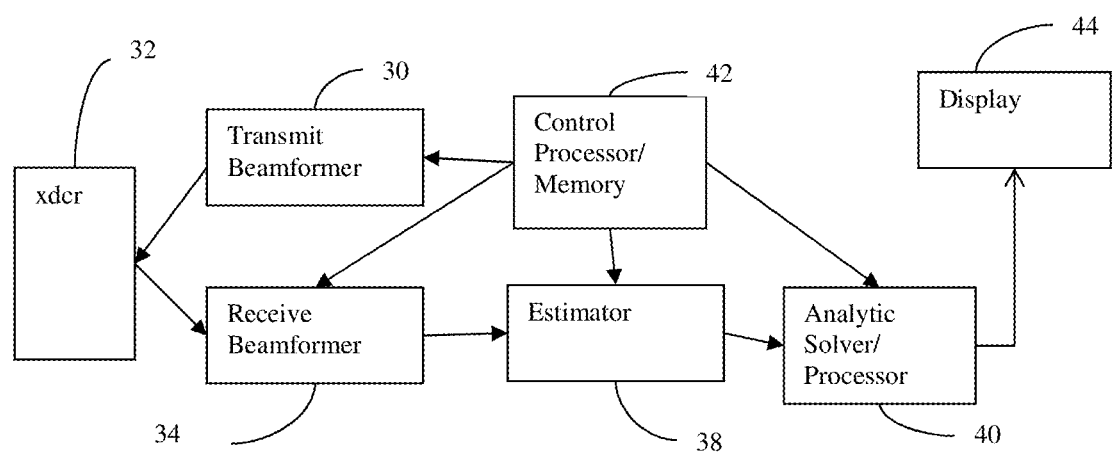
FIG. 9 is a block diagram of one embodiment of a system for color imaging with line artifact reduction.

The method of FIG. 3 is implemented by or on the system of FIG. 9, an ultrasound scanner, a processor, a workstation, a computer, or a different system. The method is performed by a medical diagnostic ultrasound imaging system. In other embodiments, the ultrasound data are acquired in real-time by an ultrasound scanner and other acts are performed in real-time or a different time by a computer, the ultrasound scanner, or another device.

Additional, different, or fewer acts may be provided. For example, acts 14, 16, and 18 are repeated more than twice. As another example, acts 22, 24, and/or 26 are not provided. In yet another example, acts for spatial and temporal filtering are included. Acts for user interaction with and activation of the ultrasound scanner are not shown, but may be provided.

The acts are performed in the order shown or other orders. Acts 14, 16, and 18 are for acquiring flow estimates from groups of simultaneous receive lines. A transmit event and a parallel or multi-beam receive event occur to scan an ensemble region once. A sequence (ensemble) of such transmit and receive events is used to acquire samples for generating a given velocity, motion, or Doppler estimate. Any number of transmit and receive event pairs to the same scan lines may be used to create an estimate. Any number of on-going scans to the same locations may be used to generate any number of estimates for those locations. The acts are repeated to scan at different locations with or without overlapping of the ensemble region for given pairs of ensembles. Data for an ensemble or sequence of scanning is collected prior to scanning for another ensemble, but interleaving in any pattern may be used. Different ensembles of transmit and responsive receive events are used to scan different portions of the field of view or region of interest. The acts 14 and 16 may be performed for different ensembles before or in parallel with performing acts 18 for other or the same ensembles.

In act 12, flow data are acquired. The flow data are velocities in FIG. 3, but may also or alternatively include energy (e.g., power) or variance. Velocity is used as an example throughout, but other measures of motion (tissue or flow) may be used.

The flow data are acquired by scanning a patient. The resulting scan data may be processed in real-time to generate an image. Alternatively, the scan data are saved and/or transmitted to a memory or over a network. The saved data are loaded from memory or received via a transmission for processing.

To acquire the flow data, the patient is scanned to acquire different sets of receive beams in act 16 responsive to spatially distinct transmissions of act 14. For example, two or more collinear receive beams are responsive to spatially distinct transmissions. The different ensembles (i.e., transmit beams along a given transmit scan line and corresponding multiple beams received along multiple receive scan lines in response to the transmit beams) cover overlapping regions. Part of the regions covered by the receive scan lines are covered by more than one ensemble. There may be complete overlap, such as where half of one ensemble is covered by half of another ensemble and the other half is covered by half of yet another ensemble. The overlap may be incomplete, such as where less than all of the region scanned by a given ensemble (transmit beam and responsive receive beams) is scanned by another ensemble. For example, ¼, ⅛, or other portion less than ½ is covered by an equal or unequal, but less than ½, portion of two surrounding (immediately adjacent) ensembles. In some of the examples below, the overlapping coverage is with collinear or co-located receive beams from different ensembles. In other embodiments, one or more of the receive scan lines from different ensembles are not collinear, but may still be interpolated to provide estimates for the same locations.

Figure 4:
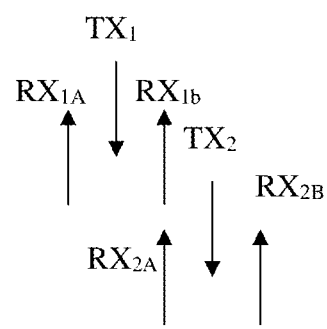
FIG. 4 is a graphical representation of one embodiment of transmit and receive beam interrelationships.

To acquire estimates for a same location from different transmit scan lines, two or more different ensembles are positioned to scan an overlapping region. Referring to FIG. 4, two sets of multiple non-collinear receive beams ($RX_{1A}$ and $RX_{1B}$, and $RX_{2A}$ and $RX_{2B}$) are formed in sequence with parallel or substantially simultaneous receive within each set in response to each transmit firing ($TX_1$ and $TX_2$, respectively) of two ensembles (1 and 2). The set of spatially distinct beams formed in parallel is called non-collinear multi-beam or multi-beam (i.e., an ensemble of simultaneous receive scan lines).

As the number of beams in a multi-beam increases (e.g., three or more), the transmit beam is wider to adequately insonify the locations of the receive beams. The wider transmit beam may cause a decrease in resolution, increase in artifacts and decrease in signal-to-noise ratio (SNR). A given scan region may be scanned more rapidly with multi-beam, resulting in a greater frame rate.

In the example of FIG. 4, one receive beam ($RX_{2A}$) from one transmit event of an ensemble is collinear with another receive beam ($RX_{1B}$) from another transmit event of another ensemble. There is a ½ overlap in the transmit beams and/or ensemble coverage. With more than two receive beams and corresponding scan lines in an ensemble, more than one scan line per pair of ensembles may be collinear or in an overlapping region whether collinear or not.

Figure 5A:
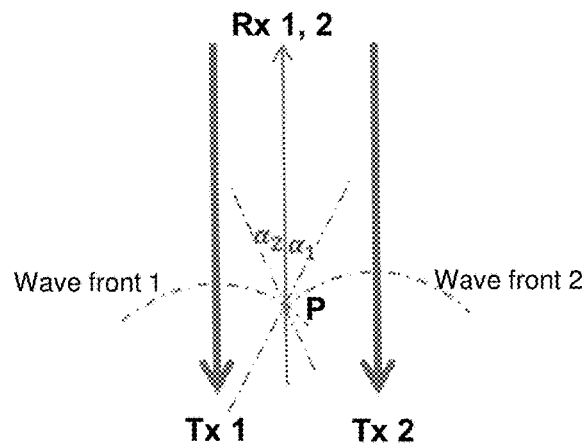
FIG. 5A shows an example position relationship between two transmit beams and collocated receive beams resulting in biases with opposite signs.
Figure 6A:
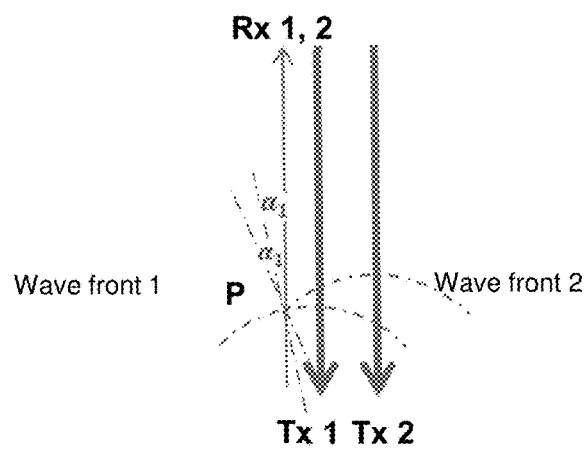
FIG. 6A shows an example position relationship between two transmit beams and collocated receive beams resulting in bias with a same sign.

At each transmit event (e.g., $TX_1$ or $TX_2$) of act 14, the transmit beamformer sends a beam. FIG. 4 shows two transmit beams generated at different times (different ensembles). FIGS. 4, 5A, and 6A each show two transmit beams and corresponding transmit scan lines for two ensembles. Each transmit beam is focused (i.e., converging wave front), unfocused (planar wave front) or defocused (diverging wave front) and propagates along a particular nominal transmit beam axis or transmit line.

At each receive event of act 16, the receive beamformer receives echoes from the object, and forms multiple beams in parallel and/or simultaneously. FIG. 4 shows two spatially distinct transmit events, and two receive beams formed in parallel or substantially simultaneously with each other in response to each transmit event. Substantially accounts for any difference in clocking or shared use of beamformer electronics. Three or more (e.g., 8, 16, 32, hundreds, or other number) receive beams may be formed simultaneously, including with or without a receive beam along the transmit line or collinear with the transmit beam. Each receive beam is dynamically focused along a particular nominal receive beam axis or receive scan line. The receive beams formed in parallel as part of an ensemble are not collinear. The non-collinear beams of a receive multi-beam have different delay and/or phase profiles. The remaining receive beamforming or echo shaping parameters, such as aperture center, aperture width, apodization type, receive filter center frequency, bandwidth, and spectral shape, may be the same or different.

FIG. 4 shows the receive multi-beams distributed in a plane, such as along an azimuth dimension with depth. The format shown is linear where the receive scan lines are parallel. In other embodiments, sector, Vector®, or other formats of the receive and/or transmit scan lines may be used. Within the azimuth plane, at least some or all of the receive beams are on one or two sides of the transmit beam. In FIG. 4, one receive beam is formed on each side (e.g., left and right) for each ensemble. Three-dimensional or volume scanning may be provided where the scan lines are distributed in azimuth and elevation, such as using a wobbler or multi-dimensional transducer array. A side of the transmit beam may be along any dimension whether in plane or spaced apart in another dimension, such as receive beams being formed on different azimuth sides but in a same elevation plane for a given ensemble.

Azimuth is along one dimension of the transducer array, such as the length. Elevation is along another, such as an orthogonal dimension of the transducer array (e.g., width). Depth or range is orthogonal to the face of the array or the distance along scan lines from the array.

The transmit and corresponding receive events are repeated to sample the region in space and in time. To sample the object in space, different ensembles with non-collinear transmit beams are used. Different portions of the scan region are sequentially scanned, as represented by the repetition of acts 14 and 16 in FIG. 3. FIG. 3 shows two ensemble regions being scanned, but three or more may be scanned. Any number of spatially different ensembles and corresponding ensemble scan regions may be used, such as the entire scan region, region of interest, or field of view being covered by 10-50 overlapping ensemble regions.

To sample the object in time, transmit-receive events with identical beamforming and pulse shaping parameters are used. For example, for each color flow mode line, multiple transmit-receive events uniformly distributed in time are used to obtain a collection of samples along each receive scan line at a pulse repetition frequency. A sequence of transmissions and receptions of an ensemble is performed to acquire the samples representing the same ensemble region over time. The collection is used to estimate a given parameter value (e.g., velocity value) for the represented locations. A moving window may be used to estimate a sequence of flow data acquired by transmitting and receiving in the ensemble to the same locations at different times.

The transmit and receive event pairs are repeated over time for each ensemble to acquire sufficient samples for estimating motion for the respective ensemble regions. Different ensembles are being used to scan different, overlapping regions. This results in samples for estimates for each ensemble region where some of the resulting estimates from different ensembles are for the same location and time. The same time is used from the user perspective despite the samples being acquired sequentially in the scan pattern. The rapidity of the scan provides a frame of estimates for all of the locations of the region of interest (motion scan region) for one time. By repeating the scanning, frames for other times are acquired.

In the example of FIG. 4, two receive beams are collinear or collocated ($RX_{1b}$ and $RX_{2a}$). Since each receive beam is on opposite sides of the respective transmit beams, the resulting velocities estimated from ensembles for the receive beams have opposite or different signed bias.

Due to the desired scan pattern and/or at an edge of a scan region, the only collinear receive beams may be on the same sides of the respective transmit scan lines. For example, FIG. 6A demonstrates when both receive beams are located on the left sides of the transmit beams. The transmit scan lines are spaced away from the receive scan line by different amounts. This may happen at an edge of a motion scan region or region of interest. To avoid transmissions and/or reception along scan lines outside the region, the transmit scan lines may be spaced in the region and away from the edge. The receive scan line or lines at and/or near the edge are all to a same side of the transmit scan lines. This arrangement may occur for other reasons than being at an edge.

In other embodiments using arbitrary combinations of velocities from collocated receive scan lines, any combination of biases may be provided such that the biases may not cancel each other out. For example, different numbers of collocated receive beams with "+" bias than "−" bias are used. Any scan pattern providing for velocity estimation along collocated receive scan lines with different spacing of transmit scan lines may be used. The transmit scan lines are spaced from the receive scan line by the same or different amounts to the same or different sides. Based on scanning for the ensemble, velocities with different bias sign and/or amounts are provided for each location along the collocated receive scan line.

In act 18, motion data are estimated for each of a plurality of locations. The estimates are created along each of the receive scan lines for each given ensemble. For a given ensemble, temporal repetition of the transmission and multi-beam reception provides samples for estimating flow. Flow values are estimated for any number of locations along each of the receive scan lines from a sequence of receptions (ensemble) along the scan lines. This estimation is repeated for each ensemble region, so estimates are provided for multiple receive scan lines of different ensemble regions.

The scanning may be performed a plurality of times in each ensemble region and a plurality of times in sequence across the ensembles to cover the entire scan region. The acts are repeated to scan different portions of the region of interest.

Scanning at different times acquires spatial samples associated with flow or motion. Any now known or later developed pulse sequences may be used within each ensemble. A sequence of at least two (flow sample count) transmissions from a same transmit scan line is provided along each receive scan line. Any pulse repetition frequency, flow sample count, and pulse repetition interval may be used. The transmissions along one line(s) may be interleaved with transmissions along another line(s). With or without interleaving, the spatial samples for a given time are acquired using transmissions from different times. The estimates from different scan lines may be acquired sequentially, but rapidly enough to represent a same time from a user perspective. Multiple scans are performed to acquire estimates for different times.

The received spatial samples within an ensemble may be clutter filtered. The clutter filtering is to condition signals in the pulse sequence for estimating motion at a given location and time. A given signal may be used for estimates representing different times, such as associated with a moving window for clutter filtering and estimation. The clutter filter removes samples associated with slow or fast movement to isolate tissue motion or fluid motion. Different filter outputs are used to estimate motion for a location at different times.

The echo responses to the transmissions of the sequence are used to estimate velocity, clutter filtered or unfiltered energy (power), and/or variance at a given time. Color data are generated from the spatial samples. Any motion data may be generated, such as velocity, energy (power), and/or variance. Doppler processing, such as autocorrelation, may be used. In other embodiments, temporal correlation may be used. Another process may be used to estimate the flow data. Color Doppler parameter values (e.g., velocity, energy, or variance values) are estimated from the spatial samples acquired at different times. "Color" is used to distinguish from spectral Doppler imaging, where the power spectrum for a range gate is estimated. The change in frequency or phase between two samples for the same location at different times indicates the velocity. A sequence of more than two samples may be used to estimate the color Doppler parameter values. Estimates are formed for different groupings of received signals, such as completely separate or independent groupings or overlapping groupings. The estimates for each grouping represent the spatial location at a given time.

The estimation is performed for the different sampled spatial locations. For example, velocities for the different locations in a plane are estimated from echoes responsive to the scanning. Multiple frames of flow data may be acquired to represent the region of interest at different times, respectively. Motion values are estimated for each of the receive beams for each of the different ensembles.

For collocated receive beams, multiple velocities are provided for the same location and time from the different ensembles. Each of these velocities is from a different ensemble and corresponding transmit scan line location. For example, Doppler velocities representing the same or adjacent locations, but estimated from different transmit beam and responsive receive multi-beams combinations, are estimated.

A processor combines the estimates associated with the different sequences of scanning using spatially distinct or non-collinear transmit beams. Any number of estimates for the same location may be combined. For example, estimates from two, three, or more different ensembles are combined to provide an estimate for a given location.

FIG. 5A shows combining two collocated beams with opposite signed bias. Rx 1 and Rx 2 are two collocated receive beams from transmit beam groups Tx1 and Tx2, respectively. The wavefronts for the transmit beams are shown as curved dash-dot lines. These wavefronts intersect the location P along the receive scan line. The angles between these receive beams and the normal direction of the echo wavefronts (receive-echo-normal) at point P are α1 and α2, as illustrated in FIG. 5A. In the example of FIG. 5A, the angles are not equal. In other embodiments, the angles are equal.

Figure 5B:
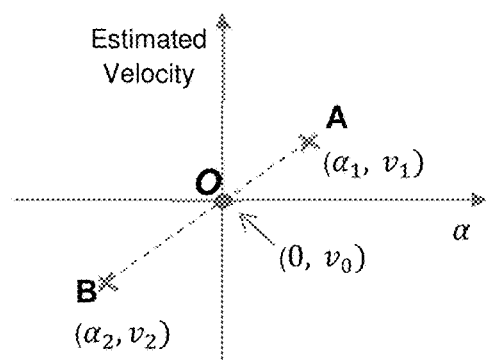
FIG. 5B shows a graph of velocity as a function of an angle between a normal to the wavefront and the collocated receive beam of FIG. 5A.

FIG. 5B shows a graph of the estimated velocity as a function of the angle. The lateral axis is the receive-echo-normal angle, and the vertical axis is the estimated velocity. The estimated velocity at P is $v_1$ from Rx 1 and $v_2$ from Rx 2, but these velocity estimates are biased. Ideally, the unbiased velocity results when the receive scan line and the transmit scan line are aligned, which is indicated by O ($\alpha=0$, $v_0$) in FIG. 5B. Thus, the problem becomes deriving $v_0$ from $v_1$ and $v_2$, where $v_0$ is the intercept of the line connecting point A and B with the zero angle axis.

Figure 6B:
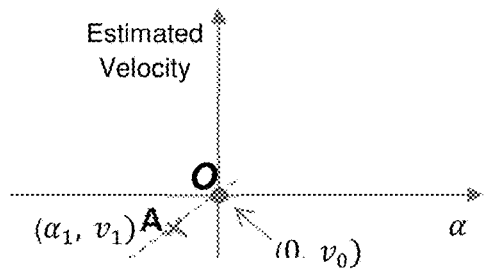
FIG. 6B shows a graph of velocity as a function of an angle between a normal to the wavefront and the collocated receive beam of FIG. 6A.

FIGS. 6A and 6B correspond to FIGS. 5A and 5B, but with the biases having a same sign due to the collocated receive scan lines being on the same side of the transmit scan lines for both ensembles. If the velocities of FIG. 5B were averaged, the biases would substantially cancel (e.g., reduction of bias by half or more). If the velocities of FIG. 6B were averaged, the biases would not cancel as much. However, the relationship to the ideal is the same. The solution stays as the intercept of line AB to the y axis. The origin of the graph of FIG. 6B indicates the velocity without bias.

Figure 7A:
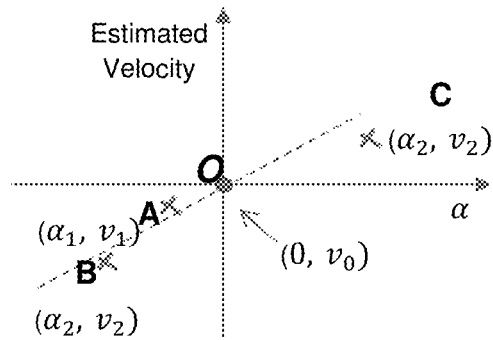
FIGS. 7A-C show example graphs of velocity as a function of angle based on arbitrary numbers of collocated receive beams.
Figure 7B:
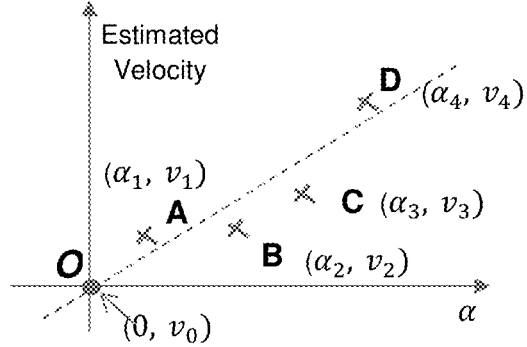
Figure 7C:
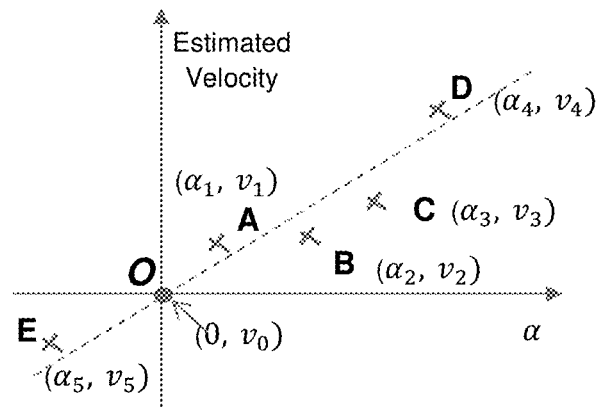

FIGS. 7A-C illustrate further examples of different numbers of collocated receive beams with different biased velocities and different angles. FIG. 7A shows estimated velocities with two velocities having a "−" signed bias and one velocity having a "+" signed bias. FIG. 7B shows estimated velocities with no velocities having a "−" signed bias and four velocities having a "+" signed bias. FIG. 7C shows estimated velocities with one velocity having a "−" signed bias and four velocities having a "+" signed bias. Other beam positions, biasing combinations of velocities, and/or number of beam positions (e.g., number of ensembles with collocated receive beams) may be used.

Referring again to FIG. 3, the processor (e.g., analytic solver, control processor, Doppler processor, or other) removes or reduces the biases in the estimated velocities. The bias may be calculated and removed. Alternatively, the bias is removed by solving for a single unbiased velocity using the multiple biased velocities for the location and time. The relative positions of the transmit scan lines to the collocated receive scan lines for the different ensembles is used to remove the bias.

Based on the information in the graph (i.e., the biased velocities and the angle), a regression is performed to determine the unbiased velocity at the location. This regression acts to remove the biases by finding the velocity without the bias. The regression combines the biased velocities from the different ensembles for the time, resulting in one estimated velocity for the location. For each location for which velocity estimates are acquired from more than one of the multiple sequences, the biases are accounted for in the velocity estimates with a linear regression model.

To analytically solve the problem, the velocity estimate, $v_{kj}$, at the $k^{th}$ output location (e.g., P) is given by the receive beam from the $j^{th}$ transmit, and the unbiased velocity estimate is $v_{k0}$. In the example of FIGS. 6A and 6B, k is P, with two (j) transmit scan lines used to estimate two velocities, $v_1$ and $v_2$. The linear regression model is established, such as by equation 1 below:

$$v_{kj} = v_{k0} + f(\alpha_{kj}) + \varepsilon_{kj}, \quad \text{(Equation 1)}$$

where $f(\ )$ is an arbitrary function representing a line or curve fit to the graph of FIG. 6B or other graph of velocity as a function of angle. $\varepsilon_{kj}$ is an error term or noise. The task here is to find $v_{k0}$ from multiple ($\alpha_{kj}$, $v_{kj}$) pairs.

The linear regression mode is used for each location. A line or curve is fit to the velocity estimates of the location in act 22 and the linear regression model is solved in act 24. The fitting and solving may be performed as one operation, such as the solution fitting the line or curve. The fitting and/or solution provides the intercept or estimated unbiased velocity at the zero angle.

The line or curve fitting of act 22 fits to the biased velocities as a function of the angles. Any number of sample points may be used for fitting, such as two (e.g., see FIGS. 5B and 6B), three (e.g., see FIG. 7A), four (e.g., see FIG. 7B), five (e.g., see FIG. 7C), or more.

In one embodiment, a line is fit as a first order linear regression model. Assuming a first order model, equation 1 becomes:

$$v_{kj} = v_{k0} + \beta_1 \cdot \alpha_{kj} + \varepsilon_{kj}, \quad \text{(Equation 2)}$$

where β is a slope of the line. The solution for $v_{k0}$ is:

$$v_{k0} = \overline{v_k} - \frac{ss_{\alpha_k v_k}}{ss_{\alpha_k}} \cdot \overline{\alpha_k} \quad \text{(Equation 3)}$$

where $\overline{v_k}$ is the velocity average of all contributing receive beams at location k, $\overline{\alpha_k}$ is the average of the receive-echo-normal angles from all contributing receive beams, $ss_{\alpha_k v_k}$ is the correlation coefficient between $\alpha_k$ and $v_k$ ($\alpha_k$ and $v_k$ are vectors of $\alpha_{kj}$ and $v_{kj}$ (all velocity-angle pairs in the graph)), and $ss_{\alpha_k}$ is the autocorrelation of $\alpha_k$. The ratio of $$\frac{ss_{\alpha_k v_k}}{ss_{\alpha_k}}$$

gives the slope β.

In another embodiment, a curve is fit as a second order linear regression model. When a second order term is considered, equation 1 becomes:

$$v_{kj} = v_{k0} + \beta_1 \cdot \alpha_{kj} + \beta_2 \cdot \alpha_{kj}^2 + \varepsilon_{kj}, \quad \text{(Equation 4)}$$

The solution is written as:

$$v_{k0} = \overline{v_k} - \frac{\begin{vmatrix} \sum_j \alpha_{kj}^4 & \sum_j \alpha_{kj}^2 v_{kj} \\ \sum_j \alpha_{kj}^3 & \sum_j \alpha_{kj} v_{kj} \end{vmatrix}}{\begin{vmatrix} \sum_j \alpha_{kj}^2 & \sum_j \alpha_{kj}^3 \\ \sum_j \alpha_{kj}^3 & \sum_j \alpha_{kj}^4 \end{vmatrix}} \cdot \overline{\alpha_k} - \frac{\begin{vmatrix} \sum_j \alpha_{kj}^2 & \sum_j \alpha_{kj}^2 v_{kj} \\ \sum_j \alpha_{kj}^3 & \sum_j \alpha_{kj} v_{kj} \end{vmatrix}}{\begin{vmatrix} \sum_j \alpha_{kj}^2 & \sum_j \alpha_{kj}^3 \\ \sum_j \alpha_{kj}^3 & \sum_j \alpha_{kj}^4 \end{vmatrix}} \cdot \overline{\alpha_k^2} \quad \text{(Equation 5)}$$

The combined velocity, $v_{k0}$, is solved for using equation 3 or 5. The line or curve fitting provides the velocity at the intercept. In the examples of FIGS. 5B, 6B, and 7A-C, the intercept is the origin in the graph. Solutions without normalization to the origin may be provided. The graph of velocity as a function of angle is used to fit a line or curve and solve for the unbiased velocity as a velocity combined from the biased velocities.

The angle is calculated using the transmit beamforming parameters for the transmit beams, a transmit propagation model, wave equations, and/or empirical testing. The angle depends on both depth and beam shape. In implementation, the angle, $\alpha_{kj}$, for each graph sample may be difficult or inefficient to calculate.

Figure 8:
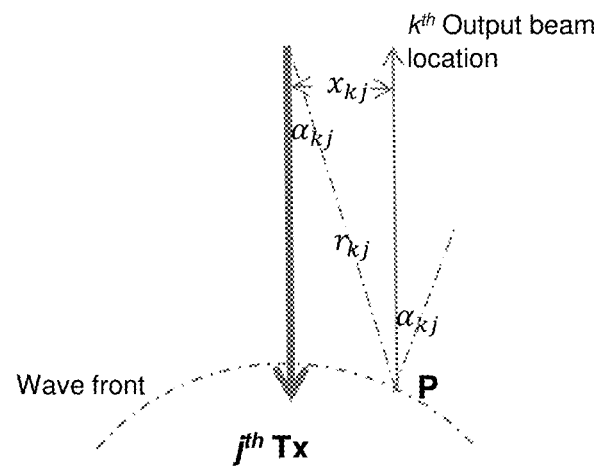
FIG. 8 illustrates a relationship between (a) the angle to the wavefront normal and the receive scan line and (b) the distance between the transmit scan line and the receive scan line.

In another embodiment, a distance is used. The distance replaces or is used to approximate the angle. The angle is approximated, as represented by:

$$\alpha_{kj} = \frac{x_{kj}}{r_{kj}}, \qquad \text{(equation 6)}$$

where $x_{kj}$ is the distance between the receive beam at the $k^{th}$ output location and $J^{th}$ transmit scan line, and $r_{kj}$ is the distance between origin of $J^{th}$ transmit scan line and P. FIG. 8 shows an example. Where the receive scan line and transmit scan line are parallel, x is the distance between the parallel lines. Where the receive scan line and transmit scan line are not parallel, the distance is measured from P on the receive scan line to the closest point along the transmit scan line. In other embodiments, the approximation is further simplified. $r_{kj}$ for all of the samples is treated as being equal, so is approximated by $r_k$. Replacing $\alpha_{kj}$ with $x_{kj}$ and $r_k$ in equations 3 and 5, $r_k$ is canceled. The solution simply replaces $\alpha_{kj}$ with $x_{kj}$ The line or curve is fit to the velocity estimates and distances of the location to the transmit scan lines. In this approach, the graphs for the linear regression model are biased velocity as a function of distances from the location to the respective transmit scan line.

The examples of FIGS. 4-7 are for planar imaging. In volume imaging, a similar approach may be used. The receive scan lines are distributed in the volume (azimuth and elevation) rather than just the plane (azimuth). The scan pattern of ensembles provides for overlap in both azimuth and elevation, providing for analytically solving for a combined velocity at a location from transmit scan lines distributed in the volume (i.e., along both azimuth and elevation). The distance is calculated in three dimensions. The graphs provide points distributed along three dimensions, so the linear regression fits a curve or surface to the points to find the intercept (velocity at the zero distance location).

In act 26 of FIG. 3, a Doppler or other motion image is generated. For example, a color Doppler or color flow image is generated. Velocities are mapped to colors, and the colors are displayed. The flow information is displayed for regions of flow, such as where sufficiently (e.g., thresholded) high velocities and/or energies occur. For other locations, B-mode, other, or no data are used for the image. In one embodiment, the color flow image is a color overlay on a B-mode image. As an alternative to color, the flow estimates may be mapped to gray scale values. In yet other alternatives, the estimates are for moving tissue, and a tissue Doppler image is generated.

The motion image is generated from the combined estimates (i.e., the unbiased estimates provided from the solution of act 24 and/or the estimates combined from the different ensembles for a same location with the biases removed). The bias corrected velocity or other bias corrected estimates are used to generate the Doppler image. For various locations represented in the image, the combined estimates (i.e., bias corrected estimate) are used. The motion values are used for some or all of the locations for which motion is displayed. The results of the solution include less bias, so the resulting image includes less line artifact. Where some estimates are not provided by the analytic solution, the resulting image is generated with estimates resulting from the linear regression and estimates free of linear regression (e.g., estimate for which only one ensemble samples the location, estimates interpolated from multiple estimates without the linear regression, and/or estimates averaged without the linear regression). By using the linear regression model for only a sub-set of receive scan lines (e.g., receive scan lines near the edge of the Doppler imaging scan region), other processes that may be more efficient may be used for other locations. Alternatively, the linear regression approach is used throughout the region of interest or all of the motion estimates. With less or no line artifact, the motion image may be used for diagnosis.

In one embodiment, the image is generated as representing a plane within the patient, such as a scan plane. A sequence of images may represent the scan plane over time. The scanning and estimation is repeated to show the motion at different times. In another embodiment, the image represents a volume. Three-dimensional rendering, such as surface rendering, volume rendering, projection rendering (e.g., maximum value), path trace rendering, or alpha blending, is performed from a given view using the motion estimates. Any now known or later developed three-dimensional rendering may be used. Multi-planar reconstructions (e.g., extracting a plurality of different imaging planes from volume information) may be used. An arbitrary planar image may be generated from estimates representing a volume.

FIG. 9 shows one embodiment of a system for motion or Doppler imaging with line artifact reduction. The system is a medical diagnostic ultrasound imaging system, but other imaging systems using multiple simultaneous receive beam scanning may be used. In other embodiments, the system is a computer, workstation, server, or other processor for operating on scan data received over a network or loaded from memory.

The system includes a transducer 32, a transmit beamformer 30, a receive beamformer 34, an estimator 38, an analytic solver or processor 40, a display 44, and a control processor and memory 42. Additional, different or fewer components may be provided. For example, a scan converter is provided. As another example, the memory is separate from the processor 42. In yet another example, the processor 42 implements the analytic solver 40.

The transducer 32 is an array of a plurality of elements. The elements are piezoelectric or capacitive membrane elements. The transducer elements transduce between acoustic and electric energies. The array is configured as a one-dimensional array, a two-dimensional array, a 1.5D array, a 1.25D array, a 1.75D array, an annular array, a multidimensional array, combinations thereof, or any other now known or later developed array. The transducer 32 connects with the transmit beamformer 30 and the receive beamformer 34 through a transmit/receive switch, but separate connections may be used in other embodiments.

Two different beamformers are shown in the system 10, a transmit beamformer 30 and the receive beamformer 34. While shown separately, the transmit and receive beamformers 30, 34 may be provided with some or all components in common. Both beamformers connect with the transducer 32.

The transmit beamformer 30 is a processor, delay, filter, waveform generator, memory, phase rotator, digital-to-analog converter, amplifier, pulser, switches, combinations thereof, or any other now known or later developed transmit beamformer components. The transmit beamformer 30 is configured as a plurality of channels for generating electrical signals of a transmit waveform for each element of a transmit aperture on the transducer 32. The waveforms have relative delay or phasing and amplitude for focusing, defocusing, or planar focusing of the acoustic energy steered along or centered at a transmit scan line. The transmit beamformer 30 includes a controller for altering an aperture (e.g. the number of active elements), an apodization profile across the plurality of channels, a delay profile across the plurality of channels, a phase profile across the plurality of channels and/or combinations thereof.

The transmit beamformer 30 is configured for broad beam transmit, such as spreading acoustic energy over an ensemble region for simultaneous receive beam formation. The broad beam is diverging (defocused, no focus, or focus behind the array or before the region of interest), converging (focus in or beyond the region of interest), or planar (infinite focus), but has a wavefront that propagates centered along a transmit scan line.

For estimating motion, the transmit beamformer 30 is configured transmit ensembles of transmit beams along each of a plurality of transmit scan lines. An ensemble of transmit beams is transmitted sequentially along each transmit scan line. The ensemble provides a flow sample count for estimating motion.

The receive beamformer 34 is a preamplifier, filter, phase rotator, delay, summer, base band filter, processor, buffers, memory, combinations thereof or other now known or later developed receive beamformer components. The receive beamformer 34 is configured into a plurality of channels for receiving electrical signals representing echoes or acoustic energy impinging on the transducer 32. Beamforming parameters including a receive aperture (e.g., the number of elements and which elements are used for receive processing), the apodization profile, a delay profile, a phase profile, or combinations thereof are applied to the receive signals for receive beamforming. For example, relative delays and amplitudes or apodization focus the acoustic energy along one or more scan lines. A control processor controls the various beamforming parameters for receive beam formation. Beamformer parameters for the receive beamformer 34 are the same or different than the transmit beamformer 30.

The receive beamformer 34 includes one or more digital or analog summers operable to combine data from different channels of the receive aperture to form one or a plurality of receive beams. Cascaded summers or a single summer may be used. In one embodiment, the beamform summer is operable to sum in-phase and quadrature channel data in a complex manner such that phase information is maintained for the formed beam. Alternatively, the beamform summer sums data amplitudes or intensities without maintaining the phase information.

For simultaneous multi-beam, the receive beamformer 34 includes circuits, channels, memories, or other components for applying different delay or phase profiles to the same received data. Multiple receive beams for a respective multiple receive scan lines are formed in response to echoes from a single transmit beam.

In response to an ensemble of transmit beams along a transmit scan line, ensembles of samples are receive beamformed along each of multiple receive scan lines. The receive beamformation of ensembles is repeated for different transmit scan lines. Some of the receive scan lines for different transmit scan lines are collocated. Samples for multiple different ensembles are provided for the collocated receive scan lines. For example, the transmit scan line of one transmit ensemble and the transmit scan line of another transmit ensemble have one or more collocated receive scan lines and are spaced from each other and the collocated receive scan lines. For some scan patterns, the collocated receive scan lines and the locations sampled along the collocated receive scan lines are on a same side of all of the transmit scan lines sharing the collocated receive scan lines. As a result of this arrangement, all of the biases in estimated velocities from the samples have the same sign or polarity. Any arbitrary combination of transmit scan lines being on a same or different sides of collocated receive scan lines may be used.

The estimator 38 is a Doppler processor, general processor, digital signal processor, control processor, application specific integrated circuit, digital circuit, digital signal processor, analog circuit, combinations thereof or other now known or later developed processor for flow or motion estimation. The estimator 38 detects any of various characteristics, such as velocity, energy (i.e. power), and/or variance.

A clutter filter may be provided for filtering the samples prior to estimation. A corner turning memory may be used to store the samples over time used to estimate flow for a given location.

In one embodiment, the estimator 38 is a Doppler processor for estimating from the phase shift. A correlator or other processor may be used. The estimator 38 outputs estimates for each location. Separate estimates are provided for each ensemble of receive scan lines. Multiple samples in a same ensemble for each location of each receive scan line are used to estimate the flows for a given time. The estimation may be repeated with a moving window to provide estimates over time for each location. The estimation is repeated for each ensemble, providing estimates for overlapping regions in response to different transmit scan line locations. The estimator 38 estimates a Doppler value for a collocated location from receive beams from one transmit ensemble and a Doppler value for the collocated location from receive beams from another transmit ensemble. Due to the receive scan lines being spaced from the transmit scan lines, the Doppler values have biases. Where the collocated receive scan lines are on a same side of the respective transmit scan lines, the estimated Doppler values have a same sign (i.e., are all biased in a same direction such as biased to all have greater magnitude or biased to all have lesser magnitude). For a given location, all estimates have biases with a same sign or some estimates have biases with one sign and others have biases with another sign.

The analytic solver 40 is a processor, circuit, digital circuit, field programmable gate array, digital signal processor, application specific integrated circuit, combinations thereof, multiplier, summer, buffer, or other device for applying a linear regression model. In one embodiment, the analytic solver 40 is implemented by the control processor 42. The analytic solver 40 is configured by hardware and/or software to combine estimates. The analytic solver 40 and/or the control processor 42 are configured to correct, at least in part, for the biases in the Doppler values.

The analytic solver 40 is configured to combine estimates from collinear receive scan lines of different ensembles or spatially distinct transmit beam locations. A combined value is determined from the estimated Doppler values for a given collocated location. The combined value is determined with an analytic solution from the biased estimated Doppler values and the distances of the location to the different transmit scan lines to which the estimated Doppler values are responsive. In one embodiment, the analytic solver 40 determines the combined value from a line or curve fit to the estimated Doppler values as a function of the distances of the transmit scan lines from the collocated location. By solving the linear regression model, the Doppler value without bias, as if the estimate was from a receive location collocated with a transmit scan line at the location, is calculated. Combined values are calculated for each of a plurality of locations along the collocated receive scan lines and/or along other collocated receive scan lines.

A filter may be provided for spatial filtering. Any residual line artifact may be removed by spatial filtering. Since some or all of the line artifact is removed by the analytic solution, less or no spatial filtering may be needed.

The locations for which estimates resulting from analytic solution are provided are on a same acoustic or scan grid. This grid may match a display grid of the display 44. Alternatively, a spatial transformation or scan conversion aligns the estimates to the display grid. The data are output as a one-, two-, or three-dimensional representation on the display 44. Other processes, such as the generation of text or graphics may also be performed for generating an image on the display 44. For example, a display dynamic range is set, filtering in space and time using a linear or nonlinear filter which may be an FIR or IIR filter or table-based is provided, and/or the signal amplitude is mapped to display values as a function of a linear or non-linear map.

The display 44 is a liquid crystal display, plasma, computer terminal, light emitting diode, projector, printer, or other a display. The display 44 is configured to display a Doppler image or sequence of Doppler images. By loading display values for the image into a display plane memory, the display values are output to the display 44 to create an image on the display 44.

The control processor 42 is a general processor, digital signal processor, field programmable gate array, application specific integrated circuit, graphics processing unit, digital processor, analog processor, circuit, or combinations thereof. The control processor 42 interacts with one or more components to control the system. Alternatively or additionally, the control processor 42 performs part of the process, such as fitting a line or curve, solving for unbiased estimates, and/or causing scanning in any pattern.

As part of the image forming process, the control processor 42 sets a scan pattern or acquisition sequence, number of simultaneous receive beams, a number of sequential beams, a number of component beams compounded together, receive multiple beam parameters, linear regression model, combinations thereof, or other now known or later developed parameters for line artifact reduction in motion imaging using multi-beam.

The instructions for implementing the processes, methods and/or techniques discussed above are provided on non-transitory computer-readable storage media or memories, such as a cache, buffer, RAM, removable media, hard drive or other computer readable storage media. The instructions are implemented on a single device, such as the control processor 42 or analytic solver 40, or a plurality of devices in a distributed manner. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, filmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for Doppler imaging, the method comprising:
    acquiring velocity estimates from different sequences of multiple simultaneous receive beam scanning for different ensembles of receive scan lines where the receive scan lines of the different sequences are in an overlapping region of a patient;
    for each location for which velocities estimates are acquired from more than one of the multiple sequences, correcting for biases in the velocity estimates with a linear regression model; and
    generating a Doppler image from the bias corrected velocity estimates.

2. The method of claim 1 wherein acquiring comprises scanning with the different sequences and estimating the velocity estimates for each of the locations represented by the receive scan lines of two or more of the sequences each having different transmit scan lines, the locations being on a same side for each of the different transmit scan lines.

3. The method of claim 1 wherein correcting as a function of the linear regression model comprises, for each location, fitting a line to the velocity estimates of the location and solving the linear regression model as a first order model with the fit line.

4. The method of claim 3 wherein fitting comprises fitting the line to the velocity estimates and distances of transmit scan lines to the location.

5. A system for Doppler imaging, the system comprising:
    a transmit beamformer configured to transmit ensembles of transmit beams along each of a plurality of transmit scan lines;
    a receive beamformer configured to receive multiple receive beams along receive scan lines in response to each of the transmit beams, at least one of the multiple receive scan lines responsive to one of the transmit ensembles being collocated with another of the multiple receive scan lines responsive to another of the transmit ensembles;
    a Doppler estimator configured to estimate Doppler values for a collocated location from receive beams from the one transmit ensemble and from the other transmit ensemble, the Doppler values having biases, respectively, with a same sign;
    a processor configured to determine a combined value from the estimated Doppler values for the collocated location; and a display configured to display a Doppler image of the combined value for the collocated location.

6. The system of claim 5 wherein the transmit scan line of the one transmit ensemble and the transmit scan line of the other transmit ensemble are spaced from the collocated location on a same side such that the biases have the same sign.

7. The system of claim 5 wherein the processor is configured to determine the combined value as an analytical solution from the estimated Doppler values for the collocated location.

8. The system of claim 5 wherein the processor is configured to determine the combined value from a line or curve fit to the estimated Doppler values as a function of distances of the transmit scan lines for the one and other transmit ensembles from the collocated location.

* * * * *